United States Patent [19]

Kaga et al.

[11] Patent Number: 5,029,581
[45] Date of Patent: Jul. 9, 1991

[54] LASER THERAPEUTIC APPARATUS

[75] Inventors: Yoshihiro Kaga; Yoshio Uno; Junji Ogawa; Kikuo Kawasaki; Hajime Fukao, all of Kanagawa, Japan

[73] Assignee: Fuji Electric Co., Ltd., Kanagawa, Japan

[21] Appl. No.: 403,896

[22] Filed: Sep. 5, 1989

Related U.S. Application Data

[63] Continuation of Ser. No. 121,954, Nov. 18, 1987, abandoned.

[30] Foreign Application Priority Data

| Nov. 19, 1986 | [JP] | Japan | 61-275641 |
| Feb. 4, 1987 | [JP] | Japan | 62-15355[U] |
| Feb. 4, 1987 | [JP] | Japan | 62-15356[U] |
| Feb. 4, 1987 | [JP] | Japan | 62-23762 |

[51] Int. Cl.$^5$ ............................................. A61N 5/00
[52] U.S. Cl. ................................................. 128/398
[58] Field of Search ............................... 606/9, 14–16; 128/395–398, 24.1, 9, 6

[56] References Cited

U.S. PATENT DOCUMENTS

| 3,831,017 | 8/1974 | Auer | 128/6 |
| 4,336,809 | 6/1982 | Clark | 128/398 |
| 4,526,170 | 7/1985 | Tanner | 128/398 |
| 4,537,193 | 8/1985 | Tanner | 128/398 |
| 4,564,011 | 1/1986 | Goldman | 128/398 |
| 4,608,980 | 9/1986 | Aihara | 606/16 |
| 4,648,892 | 3/1987 | Kittrell et al. | 128/398 |
| 4,653,495 | 3/1987 | Nanaumi | 606/9 |
| 4,712,537 | 12/1987 | Pender | 606/14 |
| 4,840,174 | 6/1989 | Gluckman | 606/16 |
| 4,850,351 | 7/1989 | Herman et al. | 128/4 |

FOREIGN PATENT DOCUMENTS

2740969 3/1979 Fed. Rep. of Germany ...... 128/398

*Primary Examiner*—Edward M. Coven
*Assistant Examiner*—Mark S. Graham
*Attorney, Agent, or Firm*—Finnegan, Henderson, Farabow, Garrett and Dunner

[57] ABSTRACT

A laser therapeutic apparatus having an oscillator for generating a laser beam, a condenser lens for condensing the laser beam radiated from the oscillator, a plurality of optical fiber cables for guiding the condensed laser beam, and a probe connected to the distal end of each of the optical fiber cables to apply the laser beam to an affected part of a human body. The probe may be detachably connected to the distal end of the optical fiber through an optical connector. A plurality of optical fibers may have their respective laser beam emergent ends dispersedly disposed over the distal end portion of a probe casing constituting the probe. There may be prepared detachable cap-shaped attachments having various sizes which are conformable with various affected parts of patients, and a selected one of the attachments may be attached to the distal end portion of the probe casing. Thus, it is possible to carry out laser therapy efficiently and effectively.

3 Claims, 5 Drawing Sheets

LASER THERAPEUTIC APPARATUS

This application is a continuation of application Ser. No. 121,954, filed Nov. 18, 1987, now abandoned.

BACKGROUND OF THE INVENTION

1. Field of the Invention

The present invention relates to a laser therapeutic apparatus designed to apply a laser beam to an affected part of a patient who is suffering from neuralgia, rheumatism, arthritis or the like to thereby relieve or cure the discomfort. More particularly, the present invention pertains to a laser therapeutic apparatus which employs an optical fiber to guide a laser beam which is applied to an affected part of a patient through a probe.

2. Description of the Related Art

Recently, one type of therapeutic apparatus that utilizes a laser beam has been put into practical use for treatment of pains or other discomforts. A typical conventional laser therapeutic apparatus has heretofore been arranged such that a laser beam emitted from a laser diode is condensed through a condenser lens, and this condensed laser beam is guided through a single optical fiber cable to a probe which is provided at the distal end of the cable and through which the laser beam is applied to an affected part of a patient to thereby treat a disease, for example, a pain.

The above-described conventional laser therapeutic apparatus suffers, however, from the following problems. The prior art apparatus comprises a single probe in association with a laser diode which defines an oscillator for generating a laser beam and a controller which controls the laser beam. Therefore, it is possible to treat only one affected part at a time. In many cases, each individual patient has a plurality of affected parts. Accordingly, the conventional laser therapeutic apparatus has the disadvantage that the time that the laser therapeutic apparatus is used per patient is disadvantageously long, which means that the apparatus cannot efficiently be used and the patient is kept lying on the bed for a disadvantageously long time.

When the probe which has become stained or broken as a result of a long time use needs to be replaced with a new one, the probe must be changed together with the optical fiber, and it is necessary in order to effect this replacement to carry out troublesome operations. For example, it is necessary to disconnect the old optical fiber and connect a new one instead within the body of the laser therapeutic apparatus. Further, since the conventional proble has a single kind of configuration, it is difficult to effectively apply the probe to any affected part throughout the patient's body and in conformity with individual therapeutic conditions. It may be a solution to the above-described problem to prepare in advance probes having various kinds of configuration which are conformable with various affected parts and therapeutic conditions and to select a probe which is conformable with a particular affected part in each treatment. However, since the probe and the body of the apparatus are directly connected through the optical fiber, it is not easy for a doctor or an operator to replace probes at the treatment site.

SUMMARY OF THE INVENTION

In view of the above-described circumstances, it is a an object of the present invention to provide a laser therapeutic apparatus which is capable of applying laser beams to a multiplicity of affected parts at a time.

It is another object of the present invention to provide a laser therapeutic apparatus which is so designed that a doctor or an operator can readily replace a probe with another on the spot without the need to change the optical fiber led from the body of the laser therapeutic apparatus.

It is still another object of the present invention to provide a laser therapeutic apparatus which is so designed that it is possible to simultaneously apply laser beams to a plurality of therapeutic points with a single probe.

It is a further object of the present invention to provide a laser therapeutic apparatus which is so designed that it is possible to effectively apply a laser beam to any affected part of a patient's body regardless of his size without the need to change the the probe.

To these ends, according to one aspect of the present invention, there is provided a laser therapeutic apparatus having an oscillator for generating a laser beam, a condenser lens for condensing the laser beam radiated from the oscillator, an optical fiber cable for guiding the condensed laser beam, and a probe connected to the distal end of the optical fiber cable to apply the laser beam to an affected part of a human body, wherein the improvement comprises a plurality of said optical fiber cables, said probe being provided at the distal end of each of the optical fiber cables.

The above-described arrangement enables a multiplicity of affected parts to be simultaneously irradiated with laser beams, and it is therefore possible to reduce the time required to treat each individual patient by a large margin. As a result, the patient is relieved from the agony that he is kept lying on the bed for a long time. In addition, the laser therapeutic apparatus is capable of simultaneously treating a remarkably increased number of patients Thus, the apparatus can be used efficiently.

According to another aspect of the present invention, there is provided a laser therapeutic apparatus having a laser beam source incorporated in a body of the apparatus and an optical fiber connected at one end thereof to the laser beam source and having the other end portion led out from the body to guide a laser beam from the laser beam source in order to apply the laser beam to an affected part of a human body to thereby treat the affected part, wherein the improvement comprises a probe for irradiating the affected part with the laser beam, the probe being detachably connected to the distal end of the optical fiber through an optical connector.

By virtue of the above-described arrangement, one probe can readily be replaced with another on the spot without the need to change the corresponding optical fiber which is led out from the body of the laser therapeutic apparatus simply by actuating the optical connector.

According to still another aspect of the present invention, there is provided a laser therapeutic apparatus having a laser beam source incorporated in a body of the apparatus, an optical fiber led out from the body, and a probe having a probe casing which covers the distal end portion of the optical fiber while retaining the laser beam emergent end of the optical fiber so that, with the distal end portion of the probe casing applied to an affected part of a human body, the affected part is irradiated with a laser beam from the laser beam source through the optical fiber, wherein the improvement comprises optical fibers for a plurality of channels having their distal end portions led and retained in the probe casing, the optical fibers having their respective laser beam emergent ends dispersedly disposed over the distal end portion of the probe casing.

This arrangement enables a plurality of therapeutic points to be simultaneously irradiated with laser beams using a single probe, so that it is possible to increase the therapeutic efficiency.

According to a further aspect of the present invention, there is provided a laser therapeutic apparatus having a laser beam source incorporated in a body of the apparatus, an optical fiber led out from the body, and a probe having a probe casing which covers the distal end portion of the optical fiber while retaining the laser beam emergent end of the optical fiber so that, with the distal end portion of the probe casing applied to an affected part of a human body, the affected part is irradiated with a laser beam from the laser beam source through the optical fiber, wherein the improvement comprises detachable cap shaped attachments having various sizes which are conformable with various affected parts of patients, a selected one of the attachments being fitted to the distal end portion of the probe casing.

By virtue of the above-described arrangement, it is possible to appropriately apply the probe to an affected part in conformity with the size of each individual patient irrespective of whether he is an adult or a child simply by selecting an attachment in accordance with the size of a particular patient without the need to change the probe casing of the probe and the optical fiber which is led out from the body of the laser therapeutic apparatus. Thus, it is possible to effectively irradiate the affected part with a laser beam.

The above and other objects, features and advantages of the present invention will become clear from the following description of the preferred embodiments thereof taken in conjunction with the accompanying drawings.

BRIEF DESCRIPTION OF THE DRAWINGS

FIGS. 8, 9 and 10 show in combination a further embodiment of the laser therapeutic apparatus according to the present invention, in which:

FIG. 8 shows the way in which an affected part is treated with the apparatus with an attachment attached to the probe casing;

FIG. 9 shows the way in which an affected part is treated with the apparatus with no attachment attached to the probe casing; and FIG. 10 is a plan view of the attachment shown in FIG. 8.

DESCRIPTION OF THE PREFERRED EMBODIMENTS

The present invention will be described hereinunder in detail with reference to the accompanying drawings.

A first embodiment of the present invention will first be explained with reference to FIGS. 1 to 3.

Figure 3:
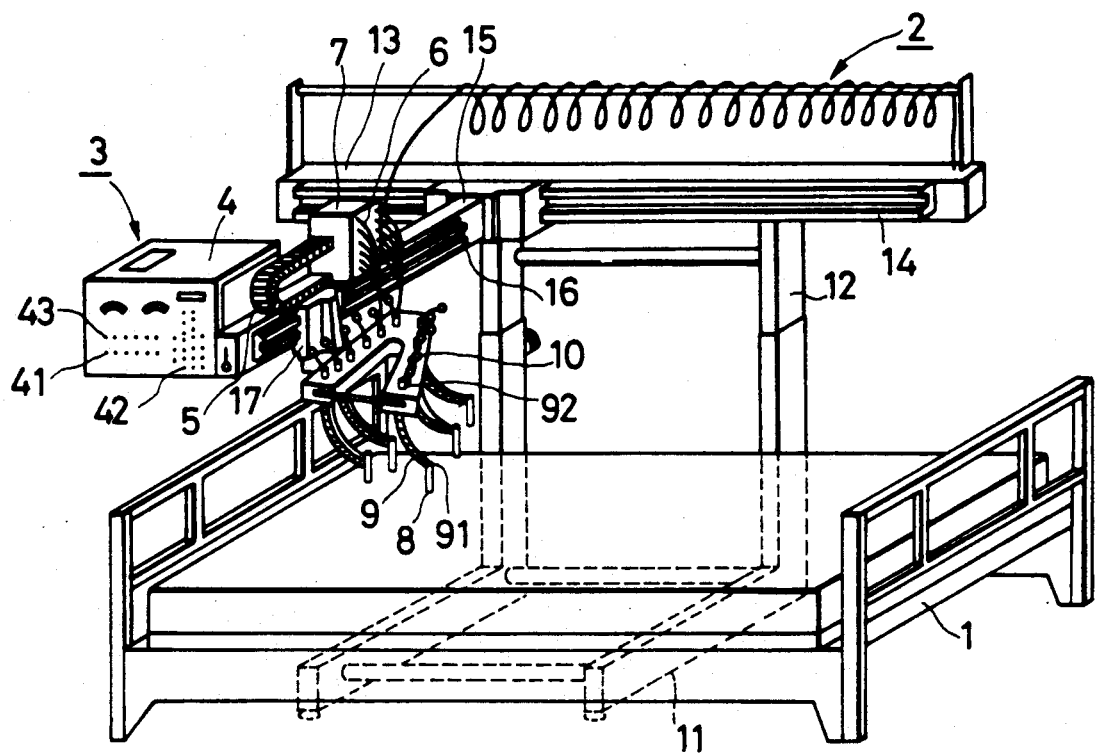
FIG. 3 is a perspective view showing the general arrangement of the laser therapeutic system including the laser therapeutic apparatus in accordance with this embodiment.

Referring first to FIG. 3, which shows the general arrangement of a laser therapeutic system including a laser therapeutic apparatus 3 according to this embodiment, the reference numeral 1 denotes a bed for a patient, and the numeral 2 denotes a carriage for movably supporting the laser therapeutic apparatus 3. The carriage 2 is arranged as follows. An X-axis frame 13 is vertically movably supported through Z-axis rails 12 on L-shaped legs 11 which are movably secured, and a Y-axis frame 15 is horizontally movably supported on the X-axis frame 13 through an X-axis rail 14. The laser therapeutic apparatus 3 is supported through a support member 17 engaged with a Y-axis rail 16 provided on the Y-axis frame 15 so that the apparatus 3 is movable in the Y-axis direction. The reference numeral 4 denotes a control box which constitutes a part of the laser therapeutic apparatus 3. On the control box 4 are disposed select switches 41, control keys 42, irradiation display lamps 43, etc. In addition, a laser diode, a condenser lens and the like, which will be described later, are disposed in the control box 4. The reference numeral 5 denotes a cable duct, and the numeral 6 denotes a multiplicity of optical fiber cables which are led out from the control box 4 in the shaped of a bundle, passed through the cable duct 5, separated from each other in a connector box 7 and have respective probes 8 connected to their distal ends. The reference numeral 9 denotes a flexible tube for covering each optical fiber cable 6, the tube 9 being connected at its proximal end to a probe table 10 and having at its distal end a probe holder 91 for retaining the corresponding probe 8. This flexible tube 9 is able to be bent in a desired shape and is fixed in a predetermined shape by means of a clamp 92 which is provided on the probe table 10.

Figure 1:
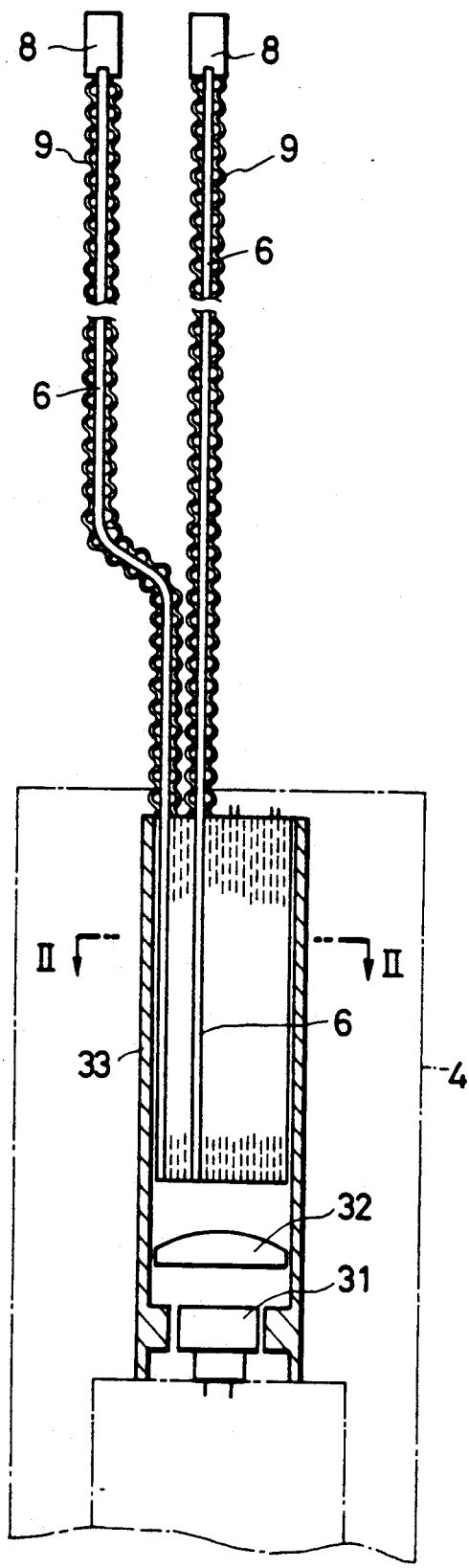
FIG. 1 is a sectional view of an essential part of one embodiment of the laser therapeutic apparatus according to the present invention.
Figure 2:
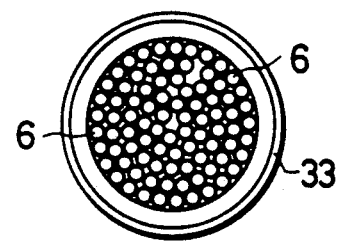
FIG. 2 is a sectional view taken along the like II—II of FIG. 1.

Referring next to FIGS. 1 and 2, which show an essential part of this embodiment, the reference numeral 31 denotes a laser diode which is provided within the control box 4 to serve as a laser beam oscillator, and the numeral 32 denotes a condenser lens. The multiplicity of optical fiber cables 6 have their outer peripheral surfaces insulated from each other, and the proximal ends of the cables 6 are tied up in a bundle within a tubular member 33. The portion of each optical fiber cable 6 which projects from the tubular member 33 is covered with the flexible tube 9. One probe 8 is provided at the distal end of each optical fiber cable 6.

In use of the laser therapeutic apparatus having the above-described arrangement, a patient lies on the bed 1, and the probes 8 are set respectively on a multiplicity of affected parts of the patient. The laser therapeutic apparatus 3 is held at the most appropriate position by actuating the carriage 2. Each probe 8 is moved onto the corresponding affected part by bending the flexible tube 9 as desired and is then fixed and held at a desired position by actuating the clamp 92. Thereafter, the select switches 41, the control keys 42 and the like which respectively correspond to the probes 8 set on the affected parts are appropriately actuated and then the power supply is turned on to cause the laser diode 31 to radiate a laser beam. The laser beam is passed through the condenser lens 32 to form a bundle of parallel rays, and the greater part of the rays divisionally enter the multiplicity of optical fiber cables 6 the end faces of which are open in front of the condenser lens 32, the laser beam then being guided to each probe 8. As a result, the laser beams are simultaneously applied to the affected parts from the multiplicity of probes 8 which are set thereon, respectively. Accordingly, a multiplicity of affected parts of the patient are simultaneously treated with laser beams within a short period of time, and the laser therapeutic apparatus is also capable of efficiently treating a multiplicity of patients.

Thus, this embodiment enables a multiplicity of affected parts to be simultaneously irradiated with laser beams, and it is therefore possible to reduce the time required to treat each individual patient by a large margin. As a result, the patient is relieved from the agony that he is kept lying on the bed for a long time. In addition, the laser therapeutic apparatus is capable of simultaneously treating a remarkably increased number of patients. Thus, the apparatus can be used efficiently.

A second embodiment of the present invention will next be described with reference to FIGS. 4 to 6.

The general arrangement of this embodiment will first be explained with reference to FIG. 4. In the figure, the reference numeral 24 denotes laser beam sources which are incorporated in a body 21 of the laser therapeutic apparatus, each laser beam source 24 being mounted on a mount 25. Optical fibers 22 for a plurality of channels are led out from the body 21 each optical fiber 22 being connected at one end thereof to the corresponding mount 25. The following various kinds of probes 27 to 51 for irradiation with laser beams are connected to the distal ends of the optical fibers 22 through optical connectors 26, respectively.

Figure 4:
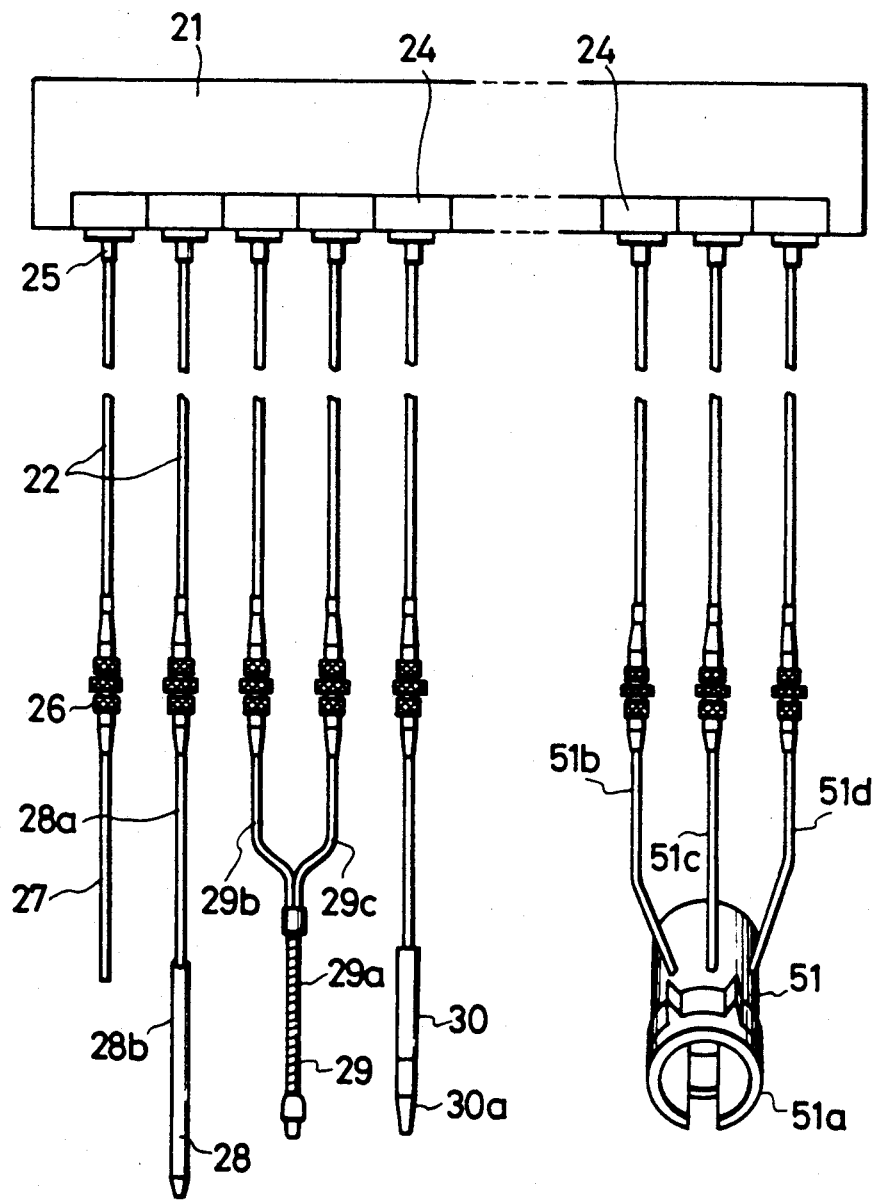
FIG. 4 shows another embodiment of the laser therapeutic apparatus according to the present invention which has a plurality of different kinds of probe.

The probes 27 to 51 are arranged in order from the left-hand side as viewed in FIG. 4. The probe 27 has a relatively simple structure which is defined by an optical fiber having its distal end subjected to an end face treatment to define a laser beam emergent end. The probe 28 is defined by an optical fiber 28a having its distal end portion retained in a protective tube 28b. The probe 29 has a structure in which a plurality of optical fibers 29b, 29c are received in a flexible protective tube 29a and laser beam emergent ends which are defined by the distal ends of the optical fibers 29b, 29c are dispersedly disposed over the distal end portion of the protective tube 29a. The probe 30 has a structure in which a condenser lens 30a is additionally attached to the distal end portion of a protective tube which is similar to the protective tube 28b of the probe 28, the lens 30a facing the laser beam emergent end of an optical fiber which is similar to the optical fiber 28a. The probe 51 comprises a band shaped retainer 51a which is to be attached to an affected part, for example, a fingertip, and which is fixed in position by means, for example, of a spring clip, and optical fibers 51b to 51d for a plurality of channels which are secured at their distal end portions to the retainer 51a. These probes having various kinds of configuration are selectively used in accordance with the position of each individual affected part and in conformity with particular therapeutic conditions. It should be noted that the probes which may be employed in the present invention are not necessarily limited to those described above and it is also possible to employ probes which have structures other than those illustrated in the figure.

Figures 5A, 5B, 5C:
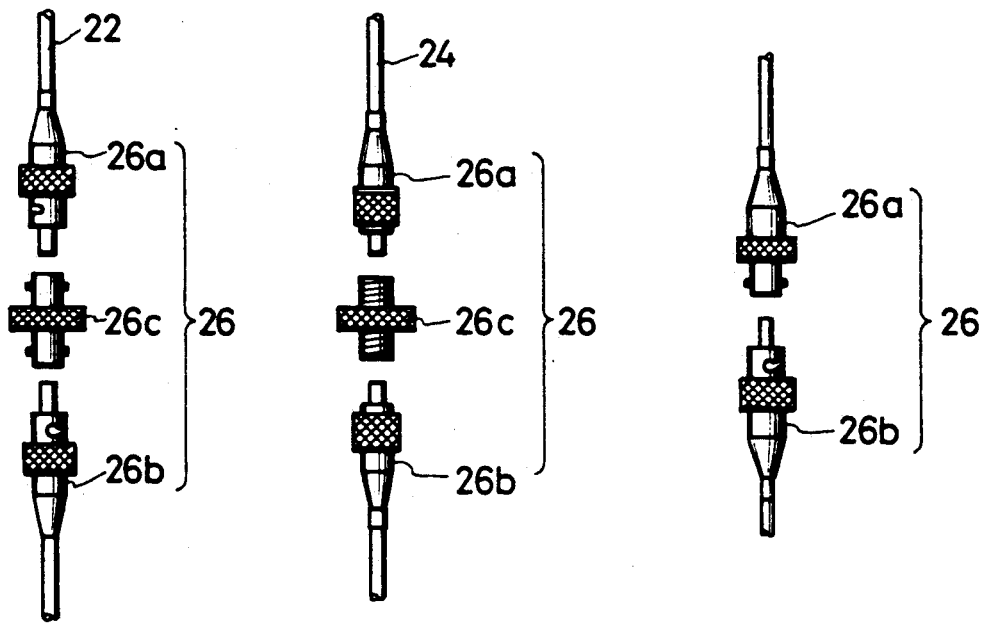
FIGS. 5a to 5c respectively show different types of optical connector which may be employed in the embodiment shown in FIG. 4.

As the optical connectors 26, various types of optical connector which are shown in FIGS. 5a to 5c may be employed. The optical connector shown in FIG. 5a has a structure in which plugs 26a and 26b are detachably coupled to an adapter 26c through a bayonet mechanism, the plugs 26a and 26b being connected respectively to the optical fiber 22 and the optical fiber which defines a probe shown in FIG. 4. In the optical connector shown in FIG. 5b, the plugs 26a and 26b are coupled to the adapter 25c through thread engagement. In the optical connector shown in FIG. 5c, the plugs 26a and 26b are directly coupled together through a bayonet mechanism without using an adapter. By actuating such an optical connector 26 when necessary, it is possible to readily disconnect and reconnect a desired optical fiber 22 and the corresponding optical fiber probe on the spot and it is therefore unnecessary to change the optical fiber 22 led out from the body 21 of the apparatus when the corresponding probe needs to be replaced with a new one.

Figure 6:
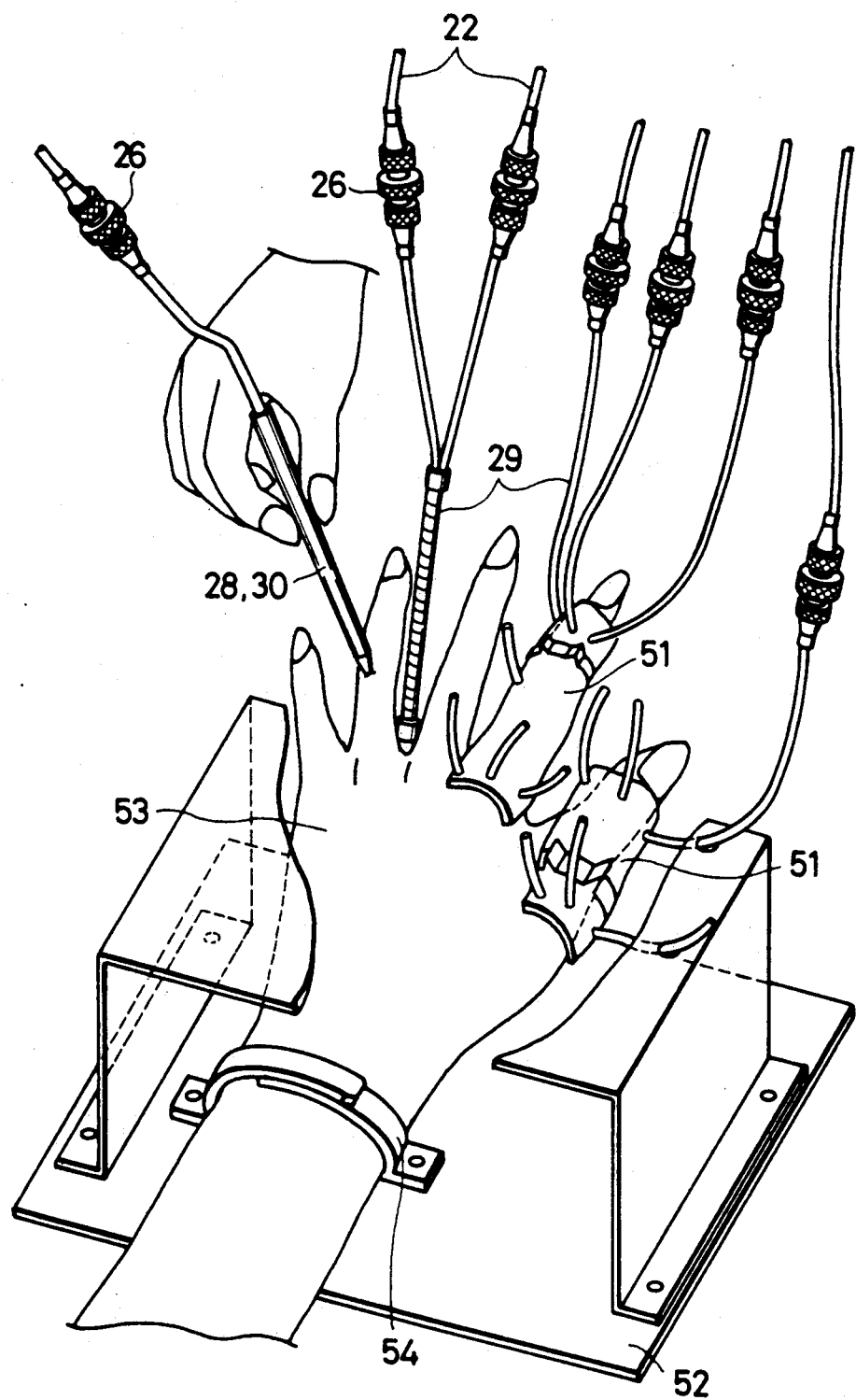
FIG. 6 shows the way in which affected parts of a patient are actually treated with the laser therapeutic apparatus in accordance with the second embodiment.

FIG. 6 shows the way in which a patient's hand is actually treated with the various kinds of probe shown in FIG. 4. In FIG. 6, the reference numeral 52 denotes a hand treating plate used to place and secure a patient's hand 53 thereon. With the wrist secured in position with a band 54, the above described various kinds of probes 28 to 51 are attached to respective affected parts of the patient as illustrated, and laser beams are then applied to the affects parts from the laser beam source in the body 21 of the apparatus through the optical fibers 22, the optical connectors 26 and the probes 28 to 51, thereby effecting laser therapy. When a probe has become broken as a result of a long time use, or when it is necessary to use a probe having a different configuration because of the position of a particular affected part or the therapeutic conditions, the probe concerned is disconnected from the corresponding optical fiber 22 by actuating the associated optical connector 26, and a new probe or a probe having a different configuration is then connected to the optical fiber 22 instead.

As described above, this embodiment enables one probe to be readily replaced with another on the spot without the need to change the corresponding optical fiber which is led out from the body of the laser therapeutic apparatus simply by actuating the associated optical connector. Accordingly, it is possible to handle the apparatus more conveniently than in the case of the conventional probe structure and enlarge the range within which the apparatus may be used.

Figure 7:
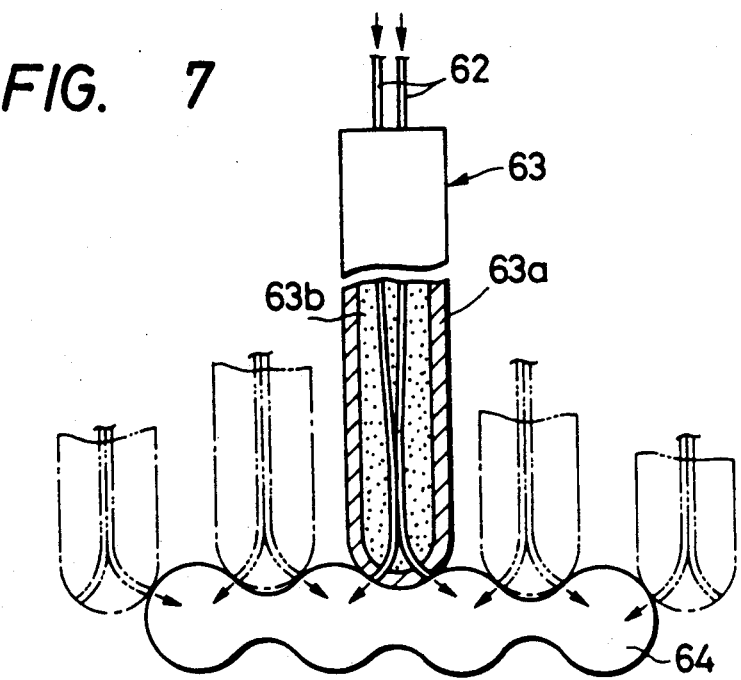
FIG. 7 shows the structure of a probe in accordance with still another embodiment of the present invention, the probe being actually used for laser therapy.

FIG. 7 shows the structure of a probe in accordance with still another embodiment of the present invention. In this embodiment, a probe 63 has a probe casing 63a, and optical fibers 62 for a plurality of channels which are led out from the body of the laser therapeutic apparatus are led into the probe casing 63a. Each optical fiber 62 is somewhat curved at its intermediate portion within the casing 63a so that the respective laser beam emergent ends of the optical fibers 62 are dispersedly disposed over the distal end face of the casing 63a. Then, the optical fibers 62 are rigidly secured within the casing 63a by means, for example, of an adhesive 63b. In the illustrated embodiment, two optical fibers 62 are retained in the probe 63, and the laser beam emergent ends of the two optical fibers 62 are separated from each other so as to extend into respective laser beam transmitting holes which are provided in two side surfaces of the spherical distal end portion of the probe casing 63a. It should be noted that it is preferable in order to minimize the propagation loss of light at the curved portion of each optical fiber 62 to select the curvature radius of the curved portion so as to be as small as possible.

To irradiate a joint portion 64 at the root of fingers with laser beams by using the probe 63 having the above-described arrangement, the probe 63 is held vertically and the distal end of the probe 63 is applied to the root portion between a pair of adjacent fingers as illustrated, and in this state, laser beams are applied to the roots of the fingers. Thus, the roots of two fingers are simultaneously irradiated with laser beams sidewardly with a single probe 63. Since the probe 63 is used in an erect position, it is possible to set another probe for other fingers in the same way without any fear of the probes interfering with each other. Accordingly, even when each of the fingers needs irradiation with a laser beam as in the case of rheumatism, it is unnecessary to carry out a laser therapy in a plurality of times but it is possible to efficiently complete a treatment within a short period of time.

As described above, this embodiment enables a plurality of therapeutic points to be simultaneously irradiated with laser beams using a single probe, so that it is possible to increase the therapeutic efficiency.

Figure 8:
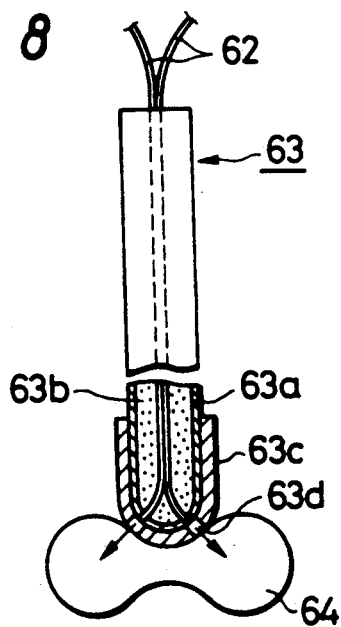

A fourth embodiment of the present invention will next be described with reference to FIGS. 8 to 10 in which the same members or portions as those shown in FIG. 7 are denoted by the same reference numerals.

In accordance with this embodiment, the probe 63 consists of a combination of a probe casing 63a which incorporates and retains the optical fibers 62 and a cap-shaped attachment 63c which is detachably fitted to the outer periphery of the distal end portion of the probe casing 63a. In this embodiment, the probe casing 63a has a relatively small external size so that the probe casing 63a is conformable with, for example, children's hands and feet. As to the attachment 63c, there are prepared a multiplicity of attachments having the same internal dimensions which are conformable with the external dimensions of the probe casing 63a and having external dimensions which are variously different from each other. Each attachment 63 has laser beam transmitting holes 63d provided in the peripheral surface of its distal end portion at positions which face the laser bean emergent ends of the optical fibers 62 retained within the probe casing 63a. It should be noted that each hole 63d has a somewhat larger diameter than the diameter of the laser beam which emerges from the optical fiber 2 with a view to preventing the laser beam from being shielded or scattered As clearly shown in FIG. 10, the attachment 63 has engagement projections 63e formed on the inner peripheral surface in order to prevent the attachment 63c from undesirably coming off the probe casing 63a.

The probe 63 having the above-described arrangement may be used as follows.

Figure 9:
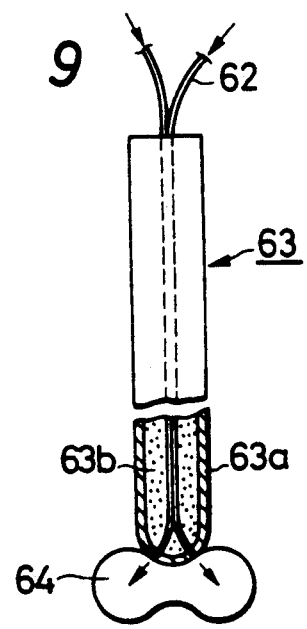
Figure 10:
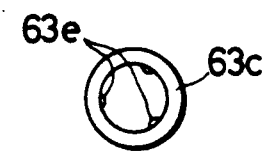

To treat a patient having small hands and feet, for example, a child, the attachment 63c is removed from the probe casing 63a, and the distal end portion of the probe casing 63a is directly applied to a joint portion 64 at the root of fingers or toes which is an affected part, as shown in FIG. 9 On the other hand, to treat a patient having a relatively large size, for example, an adult, an attachment 63c is selected in conformity with the size of the patient's hand or foot and the selected attachment 63c is fitted to the outer periphery of the distal end portion of the probe casing 63a. Then, the probe 63 is applied to an affected part of the patient's hand or foot as shown in FIG. 8.

Accordingly, it is possible to appropriately apply the probe 63 to an affected part such as a joint portion at the root of fingers or toes in conformity with the size of each individual patient irrespective of whether he is an adult or a child simply by selecting an attachment 63c in accordance with the size of a particular patient without the need to change the probe casing 63a of the probe 63 and the optical fiber 62 which is led out from the body of the laser therapeutic apparatus. Thus, it is possible to effectively irradiate the affected part with laser beams.

Although the present invention has been described through specific terms, it should be noted here that the described embodiments are not necessarily exclusive and various changes and modifications may be imparted thereto without departing from the scope of the invention which is limited solely by the appended claims.

What is claimed is:

1. A probe, for connection to a laser beam source to irradiate the skin of a patient, comprising:
   a plurality of individually encased optical fibers, each of said optical fibers having a laser beam emergent end and each being separately connectable and detachable from a laser beam source; and
   a spring clip connectable to said laser beam emergent ends for disposal around the digit of a patient to hold said laser beam emergent ends at locations remote from each other so that when the spring clip is disposed on the digit of a patient the laser beam emergent ends are disposed for irradiating various spaced apart areas of the digit.

2. A probe according to claim 1, wherein said optical fibers extend through holes in said spring clip, each of said holes having a diameter larger than the diameter of a laser beam that emerges from the optical fibers.

3. A probe according to claim 1, wherein each of said optical fibers includes a second end opposite said laser beam emergent end and an optical connecting disposed on said second end.

* * * * *